United States Patent [19]

Kao et al.

[11] 4,258,208

[45] Mar. 24, 1981

[54] PREPARATION OF ESTERS FROM ORGANIC BROMO ALKYL TELLURIUM COMPOUNDS

[75] Inventors: Jar-lin Kao; Ming N. Sheng, both of Cherry Hill, N.J.

[73] Assignee: Atlantic Richfield Company, Los Angeles, Calif.

[21] Appl. No.: 59,730

[22] Filed: Jul. 23, 1979

[51] Int. Cl.$^3$ .................... C07C 67/00; C07C 69/14; C07C 69/24
[52] U.S. Cl. .................................. 560/266; 260/550; 560/263; 568/858; 568/859; 585/641
[58] Field of Search .............................. 560/263, 266

[56] References Cited

U.S. PATENT DOCUMENTS 3,668,239  6/1972  Kallar .................................. 560/246

OTHER PUBLICATIONS

Ogawa et al., Bull. Chem. Soc., Japan, vol. 41, p. 3031, (1968).

*Primary Examiner*—Vivian Garner
*Attorney, Agent, or Firm*—Delbert E. McCaslin

[57] ABSTRACT

A process for the preparation of 2-bromoalkyl esters and vicinal glycol esters which comprises thermally decomposing at temperatures of from 100° C. to 200° C. an organic bromoalkyl tellurium compound selected from 2-bromoalkyltellurium tribromide or bis(2-bromoalkyl)tellurium dibromide, wherein the alkyl group is ethyl, propyl or butyl, in a carboxylic acid having from 1 to 4 carbon atoms which is employed as solvent as well as to supply the ester moiety to the esters produced. The esters may be converted to the respective glycol with water or an aqueous base.

6 Claims, No Drawings

PREPARATION OF ESTERS FROM ORGANIC BROMO ALKYL TELLURIUM COMPOUNDS

FIELD OF THE INVENTION

The present invention relates to a process for the preparation of 2-bromoalkyl esters and vicinal glycol esters of carboxylic acids by thermally reacting an organic tellurium compound containing bromine and a carboxylic acid.

BACKGROUND OF THE INVENTION

Numerous prior art processes have been proposed for the preparation of glycol esters of carboxylic acids by reacting an olefinically unsaturated compound such as ethylene and oxygen in the presence of a carboxylic acid and various catalyst systems including tellurium and other variable valent metal compounds together with a halogen source to provide halide ions in solution under oxidation conditions.

Literature articles, namely, Kogyo Kagaku Zassi, Vol. 73, page 1987, (1970) by M. Ogawa, C. Inone and R. Ishioka; Journ. Prakt. Chem., [4], Vol. 1, page 33 (1954) by H. Funk and Weiss and Angew. Chem. Ind. Ed. Eng., Vol. 10, page 73 (1971) by H. J. Arpe and H. Kuckertz show that tellurium tetrachloride adds across the carbon-carbon double bond in propylene to give substituted organyl tellurium trichloride, and in ethylene and in propylene when the reagents are mixed in stoichiometric ratio, to give bis(2-haloalkyl)tellurium dichlorides respectively.

In an article by M. Ogawa, Bull. Chem. Soc. Japan, Vol. 41, page 3031 (1968) and the Angew. Chem. Ind. Ed. Eng. Vol. 10, (1971) article noted above, there is described the thermal decomposition of bis(2-chloroalkyl)tellurium dichloride which when decomposed gave only olefins, various chloroalkanes, chloroolefins, hydrogen chloride and inorganic tellurium compounds and therefore provided no practical application for the preparation of glycol esters or the respective glycol such as ethylene or propylene glycol. As described hereinafter, the thermal decomposition of bis(2-chloroethyl)tellurium dichloride in acetic acid gave only a trace amount of ethylene and no glycol ester product.

There is no known prior art which describes the thermal decomposition of the organic bromoalkyl tellurium compounds of the present invention.

Contrary to the teachings of the prior art and investigative findings, it has surprisingly been discovered that organic bromo alkyl tellurium compounds selected from 2-bromoalkyltellurium tribromide and bis(2-bromoalkyl)tellurium dibromide compounds can be thermally decomposed in a carboxylic acid medium, preferably in the presence of oxygen, to give excellent yields of carboxylic acid esters, such as 2-bromoethylacetate and ethylene glycol diacetate, and at the same time essentially avoid the problems of the dissociation products encountered by prior processes.

SUMMARY OF THE INVENTION

This invention relates to a process for the preparation of 2-bromoalkyl and vicinal glycol esters by thermally decomposing at temperatures of from about 100° C. to 200° C. an organic bromo ($C_2$ to $C_4$) alkyl tellurium compound selected from 2-bromoalkyltellurium tribromide and bis(2-bromoalkyl)tellurium dibromide or mixtures thereof, in a 1 to 4 carbon atom carboxylic acid, which is, employed as solvent and as reactant to supply the ester moiety to the ester, and preferably in the presence of oxygen or an oxygen containing gas.

It is an object of this invention, therefore, to provide a process for the production of 2-bromoalkyl and vicinal glycol esters from organic bromoalkyltellurium compounds at high conversions and selectivities.

It is a further object of this invention to provide a specific process for the preparation of 2-bromoalkyl and vicinal glycol esters from specific organic bromo $C_2$ to $C_4$ alkyl tellurium di- and tribromide compounds which esters have significant industrial importance as solvents, plasticizers and for the preparation of glycols.

These and other objects and advantages of this invention will become apparent from the description of the invention which follows and from the claims.

DESCRIPTION OF THE INVENTION

In accordance with this invention 2-bromoalkyl esters and vicinal glycol esters are produced by thermally decomposing 2-bromoalkyltellurium tribromide or bis(2-bromoalkyl)tellurium dibromide or mixtures thereof, at a temperature of from 100° C. to 200° C. in a carboxylic acid medium, such as acetic acid, and preferably in the presence of oxygen or an oxygen-containing gas such as air to increase the molar ratio of vicinal glycol diester to the 2-bromoalkyl ester produced. The preparation of the 2-bromoalkyl esters and vicinal glycol esters and associated by-products employing an acetic acid (HOAc) medium as solvent and reactant may be represented by the following unbalanced postulated equations (1) and (2):

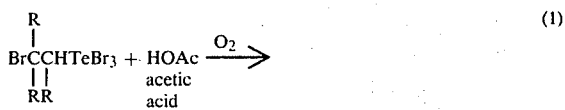

2-bromoalkyl-
tellurium
tribromide

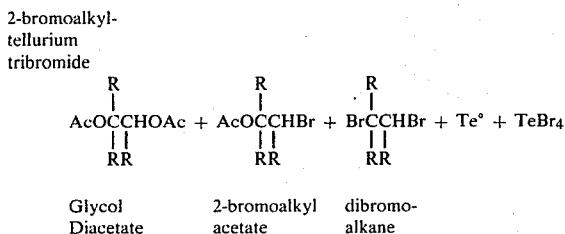

Glycol    2-bromoalkyl    dibromo-
Diacetate    acetate    alkane

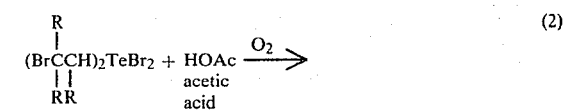

bis(2-bromoalkyl)-
tellurium dibromide

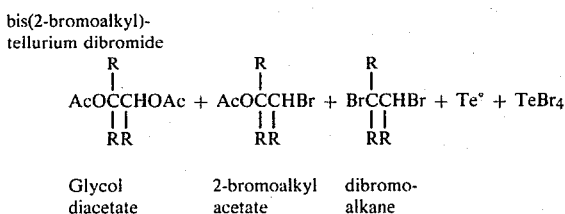

Glycol    2-bromoalkyl    dibromo-
diacetate    acetate    alkane wherein R is a hydrogen or a methyl group. The 1,2-glycol diacetate, 2-bromoalkyl acetate and 1,2-dibromoalkane products are easily converted to the glycol by reacting with water or an aqueous base.

The decomposition reaction may be carried out in any suitable reactor equipped with a gas inlet and outlet and generally with a means for agitation. A general procedure is to charge the organic bromoalkyltellurium compound and carboxylic acid, as required, into the reaction vessel and then heat the mixture to the desired temperature for the appropriate period preferably under a pressure of oxygen. The reaction may be carried out batchwise or as a continuous process and the addition of the materials may be varied to suit the particular apparatus employed. The decomposition products may be recovered by any conventional method such as filtration, distillation, etc. to effect separation of the desired products from unreacted materials, tellurium and tellurium compounds formed by the reaction, etc.

The organic bromoalkyl tellurium compounds which may be employed in the process of this invention include 2-bromoethyltellurium tribromide, bis(2-bromoethyl)tellurium dibromide, 2-bromopropyltellurium tribromide, bis(2-bromopropyl)tellurium dibromide, 2-bromobutyltellurium tribromide and bis(2-bromobutyl)tellurium dibromide.

The carboxylic acids suitable for use in the process of this invention and employed as solvent as well as reactant to supply the ester moiety to the ester produced and form, for example, an ethylene glycol diacetate and 2-bromoethyl acetate are the lower aliphatic monocarboxylic acids having from 1 to 4 carbon atoms and include formic, acetic, propionic, butyric and isobutyric acids. The monocarboxylic acid may be continuously added to the reaction system as required and when the acid is employed as solvent as well as to supply the acid moiety, it is used in excess of the stoichiometric amount required for the reaction. Generally a commercial or technical grade of acid, i.e., acids having about 80 weight percent or higher acid concentration, is employed although lower concentrations may be used.

If desired acetonitrile which is inert to the reaction system may be used as a solvent in addition to the acid reactant. When acetonitrile is employed as solvent, the acid should be employed in at least the stoichiometric equivalent required to prepare the ester.

The oxygen which is preferably employed in the process of this invention may be in the concentrated form or as an oxygen-containing gas such as air or oxygen diluted with an inert gas such as nitrogen or carbon dioxide, etc. The oxygen pressures employed will generally be between about atmospheric pressure and 100 psig. Higher oxygen pressures may be employed but at pressures such that explosive mixtures with the organic compound is avoided. Subatmospheric pressures may be used but do not appear to provide any process advantage.

The decomposition reaction will proceed at temperatures of from about 100° C. to 200° C. and are preferably maintained at between about 135° C. and 175° C. to obtain the most convenient rate of reaction. Heating and/or cooling means may be employed interior or exterior of the reaction to maintain the temperature within the desired range.

The time of reaction is generally dependent on the organic bromoalkyltellurium compound being decomposed, temperature and type of equipment employed. Generally between about ½ hour to 3 hours are required to obtain the desired conversion and selectivity to the 2-bromoalkyl acetate or vicinal glycol diacetate but shorter or longer reaction times may be employed. Reaction times will vary dependent on whether the process is continuous, semi-continuous or batch.

The following Examples are provided to illustrate the invention in accordance with the principles of this invention but are not to be construed as limiting the invention in any way except as indicated by the appended claims.

EXAMPLE 1

Preparation of Bis(2-chloroethyl)tellurium dichloride

Bis(2-chloroethyl)tellurium dichloride was prepared by the procedure set forth in Journ. Prakt. Chem., [4], Vol. 1, page 33 (1954) by Funk and Weiss noted hereinabove.

Into a 500 ml. stirred stainless steel autoclave there was introduced 16.9 g. of tellurium tetrachoride, 140.0 g. of acetonitrile and 400 psig. ethylene. The mixture was reacted with stirring for 3 hours at a temperature of 24° C. after which the reaction product of 20.1 g. (99 mole percent based on the TeCl$_4$) was isolated by filtration.

EXAMPLE 2

Preparation of Bis(2-bromoethyl)tellurium Dibromide

Bis(2-bromoethyl)tellurium dibromide was prepared by a procedure similar to Example 1 by reacting 28 g. of tellurium tetrabromide in 140.0 g. of acetonitrile solvent with 400 psig of ethylene in a 500 ml. stirred stainless steel autoclave at 21° C.–24° C. for a period of 3 hours. A 90 mole percent yield of product was obtained which by elemental analyses and $^{13}$CNMR spectroscopy gave the following:

|  | C | H | Te | Br |
|---|---|---|---|---|
| Experimental | 9.5% | 1.6% | 25.9% | 62.9% |
| Theoretical* | 9.5% | 1.6% | 25.4% | 63.5% |

*Based on the formula C$_4$H$_8$Br$_4$Te
$^{13}$CNMR Spectrum (DMSO-d$_6$)
TeCH$_2$ - 39.6 ppm.
BrCH$_2$ - 29.7 ppm.

EXAMPLE 3

Preparation of 2-bromoethyltellurium tribromide 2-bromoethyltellurium tribromide was prepared as follows:

Into a 500 ml. stirred stainless steel autoclave there was introduced 18.0 g. of tellurium tetrabromide, 12.5 g. of hydrobromic acid (48 weight percent), 137.5 g. of glacial acetic acid and 400 psig of ethylene. The solution mixture was reacted with stirring for 3 hours at a temperature of 25° C. The reaction product (85 mole percent yield) was isolated by evaporating the reaction mixture at 40° C./1. mm Hg. and recrystallizing the resulting residue from chloroform and tetrahydrofuran. Elemental analyses and $^{13}$CNMR spectroscopy of the reaction product gave the following:

|  | C | H | Te | Br |
|---|---|---|---|---|
| Experimental | 5.4% | 1.1% | 25.7% | 65.7% |
| Theoretical** | 5.1% | 0.9% | 26.8% | 67.3% |

**Based on formula C$_2$H$_4$Br$_4$Te
$^{13}$CNMR Spectrum (DMSO-d$_6$)
TeCH$_2$ - 56.1 ppm.
BrCH$_2$ - 29.7 ppm.

EXAMPLE 4

1.05 g. (2.09 mmoles) of bis(2-bromoethyl)-tellurium dibromide, from Example 2, along with 4.0 g. glacial acetic acid (99.5 percent) was charged to a "Fisher- Porter" 35 ml. glass tube reactor equipped with a gas inlet and outlet tube, a pressure gauge and relief valve and a magnetic stirrer. The mixture was heated at a temperature of 150° C. under 16 psig oxygen with stirring for 1 hour. The reaction mixture was cooled and the products analyzed by gas liquid partition chromatograph (glpc.) showed 3.10 mmoles of ethylene glycol diacetate, 0.79 mmoles of 2-bromoethylacetate, 0.12 mmoles ethylene dibromide and a trace amount of ethylene. Based on stoichiometry that one mole of bis(2-bromoethyl)tellurium dibromide yields two moles of ethylene glycol precursors, i.e., ethylene glycol diacetate, 2-bromoethylacetate and dibromoethane, the mass balance was calculated to be 96 mole percent.

EXAMPLE 5

In Example 5 the procedure and general operating conditions as employed in Example 4 was repeated using bis(2-bromoethyl)tellurium dibromide, except that nitrogen was employed instead of oxygen. Analysis of the reaction products by gas liquid partition chromatography (glpc) showed 0.30 mmoles of ethylene glycol diacetate, 2.04 mmoles of 2-bromoethylacetate, 1.06 mmoles of ethylene dibromide and a trace amount of ethylene. In comparison with Example 4 above it is shown that the addition of oxygen to the reaction increased the mole ratio of ethylene glycol diacetate to 2-bromoethyl acetate.

conversion and selectivities determined by glpc are summarized in Table 1.

TABLE 1

| Example No. | 7 | 8 | 9 | 10 | 11 | 12 |
|---|---|---|---|---|---|---|
| Reaction Time (min.) | 5 | 10 | 20 | 40 | 60 | 120 |
| % Conversion* | 70 | 92 | 98 | 100 | 98 | 97 |
| Mole % Selectivity** | | | | | | |
| to Ethylene | 18.5 | 8.8 | trace | trace | trace | trace |
| to Ethylene Dibromide | 4.9 | 1.4 | 1.1 | 1.5 | 1.2 | 1.2 |
| to 2-bromoethyl acetate | 40.9 | 30.3 | 12.0 | 9.2 | 6.1 | 5.3 |
| to ethylene glycol diacetate | 34.7 | 58.3 | 82.0 | 83.6 | 85.7 | 88.0 |
| to ethylene glycol monoacetate | 0.9 | 1.2 | 4.8 | 5.6 | 7.0 | 5.5 |

*% Conversion = $\dfrac{\text{Total products (mmoles) determined by glpc}}{2 \times (BrCH_2CH_2)_2TeBr_2 \text{ (mmoles)}} \times 100$

**% Selectivity = $\dfrac{\text{Products (mmoles)}}{2 \times (BrCH_2CH_2)_2TeBr_2 \text{ (mmoles)}} \times 100$

EXAMPLES 13–18

In Examples 13 to 18 which follow in Table form, the procedure of Example 4 was repeated using, unless noted 2.00 g. of bis(2-bromoethyl)tellurium dibromide, prepared according to the procedure shown in Example 2 and 8.00 g. of a carboxylic acid at a reaction temperature of 135° C. for 1 hour with various acid-solvent and oxygen pressures. The conditions and analytical (glpc) results are summarized in Table 2.

TABLE 2

| Example No. | 13[1] | 14 | 15 | 16 | 17 | 18 |
|---|---|---|---|---|---|---|
| $CH_3CN$ (Inert Solvent) | 4.00 | 2.00 | None | None | None | None |
| Carboxylic Acid | None | $HCO_2H$ | $HCO_2H$ | $CH_3CO_2H$ | $CH_3CH_2CO_2H$ | $CH_3(CH_2)_2CO_2H$ |
| Oxygen (psig) | 16 | 50 | 16 | 50 | 16 | 16 |
| Reaction Products (mmoles) | | | | | | |
| Ethylene | 0.17 | 0.65 | 1.78 | trace | trace | trace |
| Ethylene Dibromide | 0.05 | 0.81 | 0.83 | 0.24 | 0.22 | 0.25 |
| 2-Bromoethyl Formate | None | 3.16 | 3.39 | | | |
| Ethylene Glycol Diformate | None | 3.38 | 1.97 | | | |
| Ethylene Glycol Monoformate | None | 0.25 | 0.28 | | | |
| 2-Bromoethyl Acetate | | | | 1.40 | | |
| Ethylene Glycol Diacetate | | | | 6.10 | | |
| Ethylene Glycol Monoacetate | | | | 0.20 | | |
| 2-Bromoethyl Propionate | | | | | 1.55 | |
| Ethylene Glycol Dipropionate | | | | | 5.97 | |
| Ethylene Glycol Monopropionate | | | | | 0.01 | |
| 2-Bromoethyl Butyrate | | | | | | 1.51 |
| Ethylene Glycol Dibutyrate | | | | | | 5.95 |
| Ethylene Glycol Monobutyrate | | | | | | 0.02 |

[1] 1.00 g. bis(2-bromoethyl)tellurium dibromide employed.

EXAMPLE 6

The experimental procedure of Example 4 was carried out employing 1.00 g. (2.80 mmoles) of 2-bromoethyltellurium tribromide, from Example 3 and 4.00 g. (66.61 mmoles) of glacial acetic acid. The mixture was heated at 150° C. under 16 psig oxygen for 1 hour. Analysis of the reaction product (by glpc) showed 1.68 mmoles of ethylene glycol diacetate, 0.12 mmoles of 2-bromoethyl acetate, 0.07 mmoles of ethylene dibromide and a trace amount of ethylene.

EXAMPLES 7–12

In Examples 7 to 12 which follow in Table form, the experimental procedure used in Example 4 was repeated employing 1.00 g. bis(2-bromoethyl)tellurium dibromide, 4.00 g. glacial acetic acid at a reaction temperature of 135° C. under 16 psig oxygen with a variation in reaction times to show the effect on product distribution. The experimental results giving percent

EXAMPLE 19

The procedure of Example 2 was followed to prepare bis(2-bromopropyl)tellurium dibromide by reacting 28.0 g. of tellurium tetrabromide in 140.0 g. of acetonitrile solvent with 15 g. of propylene in a 500 ml. stirred stainless steel autoclave at a temperature of 21° C. to 25° C. for a period of 4 hours. A 90 mole percent yield of product was obtained.

2.0 g. of the bis(2-bromopropyl)tellurium dibromide along with 10.0 g. of glacial acetic acid was reacted at a temperature of 150° C. under 20 psig oxygen for 1 hour according to the method described in Example 4. Glpc analysis of the reaction product showed a 95 percent conversion with selectivities of 5 mole percent 1,2-dibromopropane, 15 mole percent 2-bromopropyl acetate and 80 mole percent 1,2-diacetoxypropane.

EXAMPLE 20

The procedure of Example 2 was followed to prepare bis(2-bromobutyl)tellurium dibromide by reacting 28.0 g. of tellurium tetrabromide with 20 g. of 1-butene in 140.0 g. of acetonitrile solvent at a temperature of 23° C. to 25° C. for a period of 3 hours. An 85 mole percent yield of bis(2-bromobutyl)tellurium dibromide was obtained.

1.0 g. of the bis(2-bromobutyl)tellurium dibromide and 5.0 g. of glacial acetic acid were reacted at a temperature of 150° C. under 20 psig oxygen pressure for 1 hour according to the method described in Example 4. Analysis (glpc) of the reaction products showed a 94 mole percent conversion with selectivities of 3 percent 1,2-dibromobutane, 18 percent 2-bromobutyl acetate and 79 percent 1,2-diacetoxybutane.

EXAMPLE 21 (comparative)

The method of Example 4 was repeated except that 1.05 g. of bis(2-chloroethyl)tellurium dichloride, prepared according to the procedure of Example 1, was employed instead of the corresponding dibromide compound. The reaction was carried out at 150° C. under 16 psig oxygen with stirring for 1 hour. Analysis showed a trace of ethylene. 90 mole percent of the original bis(2-chloroethyl)tellurium dichloride was recovered by filtration. No decomposition to the diacetate ester was detected.

We claim:

1. A process for the preparation of 2-bromoalkyl esters which comprises thermally decomposing, at a temperature in the range of from about 100° C. to 200° C., an organic bromo alkyltellurium compound selected from 2-bromoalkyltellurium tribromide having the formula

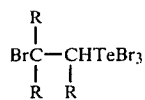

and bis(2-bromoalkyl)tellurium dibromide having the formula

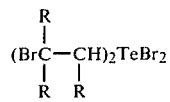

or mixtures thereof, wherein R is hydrogen or a methyl group, at least one R being hydrogen, in the presence of a lower aliphatic monocarboxylic acid selected from the group consisting of formic, acetic, propionic, butyric and isobutyric acid and in the absence of oxygen or an oxygen-containing gas and recovering the desired ester.

2. A process according to claim 1 wherein the organic bromoalkyltellurium compound is selected from 2-bromoethyltellurium tribromide, bis(2-bromoethyl)tellurium dibromide, bis(2-bromopropyl)tellurium dibromide and bis(2-bromobutyl)-tellurium dibromide.

3. A process according to claim 1 wherein the reaction is carried out in the presence of acetonitrile as solvent in addition to the monocarboxylic acid.

4. A process according to claim 1 wherein the decomposition reaction is carried out at a temperature in the range of from about 135° C. to 175° C.

5. A process for the preparation of 2-bromoethylacetate which comprises thermally decomposing at a temperature of between about 135° C. to 175° C. 2-bromoethyltellurium tribromide in an acetic acid medium in the absence of oxygen or an oxygen-containing gas.

6. A process for the preparation of 2-bromoethylacetate which comprises thermally decomposing at a temperature of between about 135° C. to 175° C. bis(2-bromoethyl)tellurium dibromide in an acetic acid medium in the absence of oxygen or an oxygen-containing gas.

* * * * *